United States Patent [19]

Bates et al.

[11] Patent Number: 4,958,625
[45] Date of Patent: Sep. 25, 1990

[54] BIOPSY NEEDLE INSTRUMENT

[75] Inventors: James S. Bates; Thomas P. Clement, both of Bloomington; Darrell W. White, Spencer, all of Ind.

[73] Assignee: Boston Scientific Corporation, Watertown, Mass.

[21] Appl. No.: 381,780

[22] Filed: Jul. 18, 1989

[51] Int. Cl.$^5$ ............................................. A61B 10/00
[52] U.S. Cl. .................................. 128/754; 128/749; 128/751; 606/167; 606/170
[58] Field of Search ....................... 128/749, 751–754; 606/167, 170

[56] References Cited

U.S. PATENT DOCUMENTS

| | | |
|---|---|---|
| 1,867,624 | 7/1932 | Hoffman . |
| 3,175,554 | 3/1965 | Stewart . |
| 3,595,217 | 7/1971 | Rheinfrank . |
| 3,995,619 | 12/1976 | Glatzer . |
| 4,178,810 | 12/1979 | Takahashi . |
| 4,402,324 | 9/1983 | Lindgren et al. . |
| 4,461,305 | 7/1984 | Cibley . |
| 4,476,864 | 10/1984 | Tezel . |
| 4,570,632 | 2/1986 | Woods . |
| 4,600,014 | 7/1986 | Beraha . |
| 4,609,370 | 9/1986 | Morrison . |
| 4,685,904 | 8/1987 | Krebs . |
| 4,699,154 | 10/1987 | Lindgren .............................. 128/754 |
| 4,702,261 | 10/1987 | Cornell et al. . |
| 4,733,671 | 3/1988 | Mehl .................................... 128/754 |
| 4,735,215 | 4/1988 | Goto et al. . |
| 4,766,907 | 8/1988 | de Groot et al. . |
| 4,776,346 | 10/1988 | Beraha et al. ...................... 128/754 |
| 4,790,329 | 12/1988 | Simon ................................. 128/749 |
| 4,881,551 | 11/1989 | Taylor ................................ 128/754 |
| 4,893,635 | 1/1990 | de Groot et al. ................... 128/754 |
| 4,903,709 | 2/1990 | Skinner .............................. 128/754 |

FOREIGN PATENT DOCUMENTS

| | | |
|---|---|---|
| 0010321 | 10/1979 | European Pat. Off. . |
| 48382 | 1/1970 | Fed. Rep. of Germany . |
| 141108 | 4/1980 | German Democratic Rep. . |
| 175611 | 12/1965 | U.S.S.R. . |
| WO8300112 | 1/1983 | World Int. Prop. O. . |
| WO8303343 | 10/1983 | World Int. Prop. O. . |

OTHER PUBLICATIONS

Meditech Brochure, "Introducing Biopty Automatic Biopsy System", 7/86.
Travenol Trucut Disposable Biopsy Needle, Brochure.
Radiplast, Brochure.
Van-Tech Products, Micro Vasive, Products for Endourology, "Single Puncture Prostatic Biopsy Needle".
P. G. Lindgren, "Percutaneous Needle Biopsy", Acta Radiologica Diagnosis, Nov. 1982, pp. 653–656.

Primary Examiner—Robert A. Hafer
Assistant Examiner—Kerry Owens
Attorney, Agent, or Firm—Fish & Richardson

[57] ABSTRACT

A biopsy needle instrument has selectable locking means to permit or prevent the projection of a cannula and a stylet and separate loading members allowing the cannula and stylet to be loaded separately and yet fired sequentially using a single button. Another embodiment of the invention permits the independent firing of the stylet and the cannula.

15 Claims, 4 Drawing Sheets

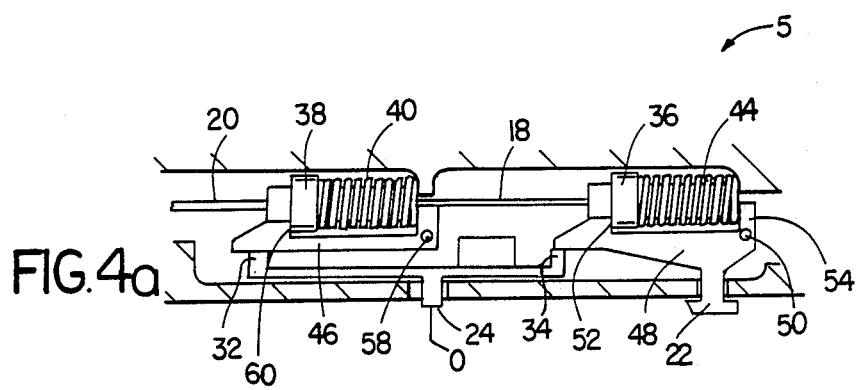
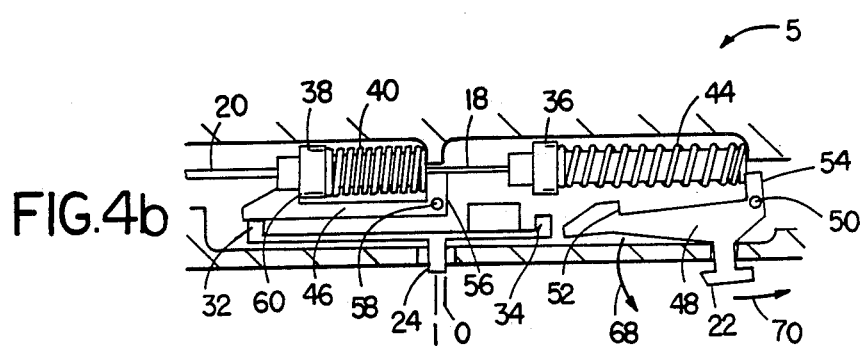
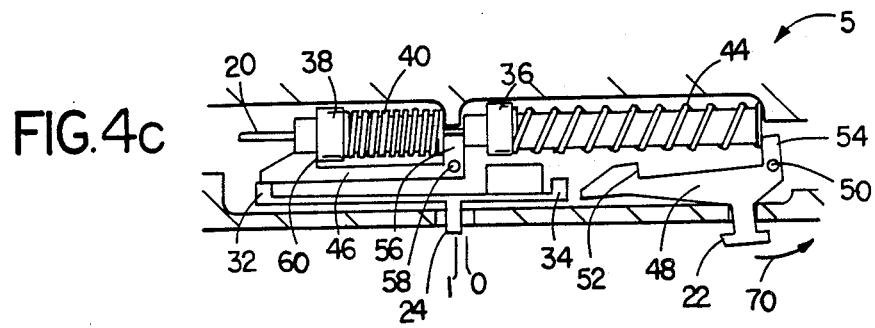
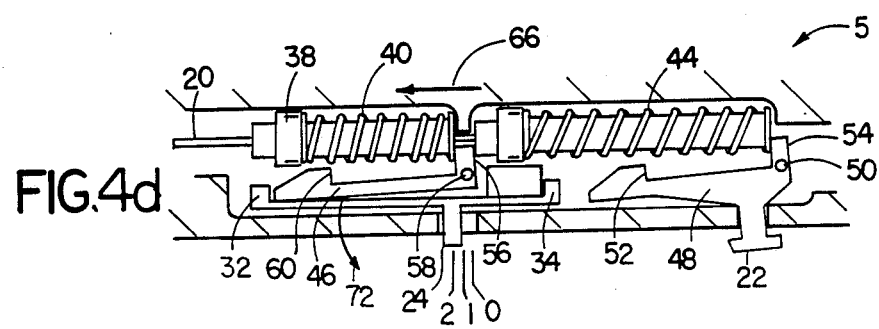

BIOPSY NEEDLE INSTRUMENT

BACKGROUND OF THE INVENTION

The invention relates to the field of surgical biopsy instruments.

A biopsy instrument is frequently used to obtain a piece of tissue for microscopic examination to determine malignancy, while subjecting the patient to the least trauma. Typically, the instrument consists of a long, thin probe, termed a stylet, within a close-fitting hollow needle, termed a cannula. The stylet and cannula are contained within a firing device that first projects the stylet into the tumor, followed immediately by the cannula. The stylet has a notch into which tissue will prolapse when the stylet enters the tumor. As the cannula slides over the stylet, a small piece of tissue is then severed from the tumor mass and captured within the notch of the stylet. The instrument is then withdrawn and the piece of tissue removed from the stylet.

Lindgren, U.S. Pat. No. 4,699,154, describes a biopsy needle instrument which projects the stylet and the cannula sequentially when the firing button is pushed. That instrument requires that the physician load both the stylet and the cannula at the same time by compressing the stylet and cannula springs simultaneously.

SUMMARY OF THE INVENTION

In one embodiment of the invention, the biopsy needle instrument comprises a selectable locking means, movable between two positions including a first safety position to prevent projection of the stylet and cannula, and a second position to permit projection of the stylet and the immediate sequential projection of the cannula.

In another embodiment, the biopsy needle comprises a selectable locking means movable also to a third or intermediate position which allows the stylet to be projected separately from the cannula. This arrangement permits a user to determine if the stylet is in the correct location prior to projecting the cannula. In this way, if the stylet misses the tumor, the cannula is not projected, thereby avoiding unnecessary damage to healthy tissue.

Another aspect of both embodiments is the ability to load the cannula and stylet separately, and yet fire them sequentially using a single button. In this way, the physician is not required to work simultaneously against two stiff springs in loading the instrument for use.

BRIEF DESCRIPTION OF THE DRAWING

This invention is pointed out with particularity in the appended claims. The above and further advantages of this invention may be better understood by referring to the following description taken in conjunction with the accompanying drawings in which:

FIG. 1a is a side view of the biopsy needle instrument of FIG. 1 in which the stylet and cannula are projected automatically in succession, while FIG. 1c is an enlarged view of the forward end of the cannula and stylet of FIG. 1;

FIG. 2 is a cross-sectional view taken at A—A of FIG. 1a;

FIGS. 4(a) through 4(d) are cross-sectional side views of the firing mechanism of another embodiment of the invention which permits the separate projection of stylet and cannula, in FIG. 4a the selector switch is in a first safety position; in FIG. 4b the selector switch is in position to fire the stylet separately from the cannula and the stylet is firing; in FIG. 4c the stylet fully projected, and in FIG. 4d the selector switch is in position to fire the cannula and the cannula is firing.

DESCRIPTION OF THE PREFERRED EMBODIMENTS

Structure

Figure 1:
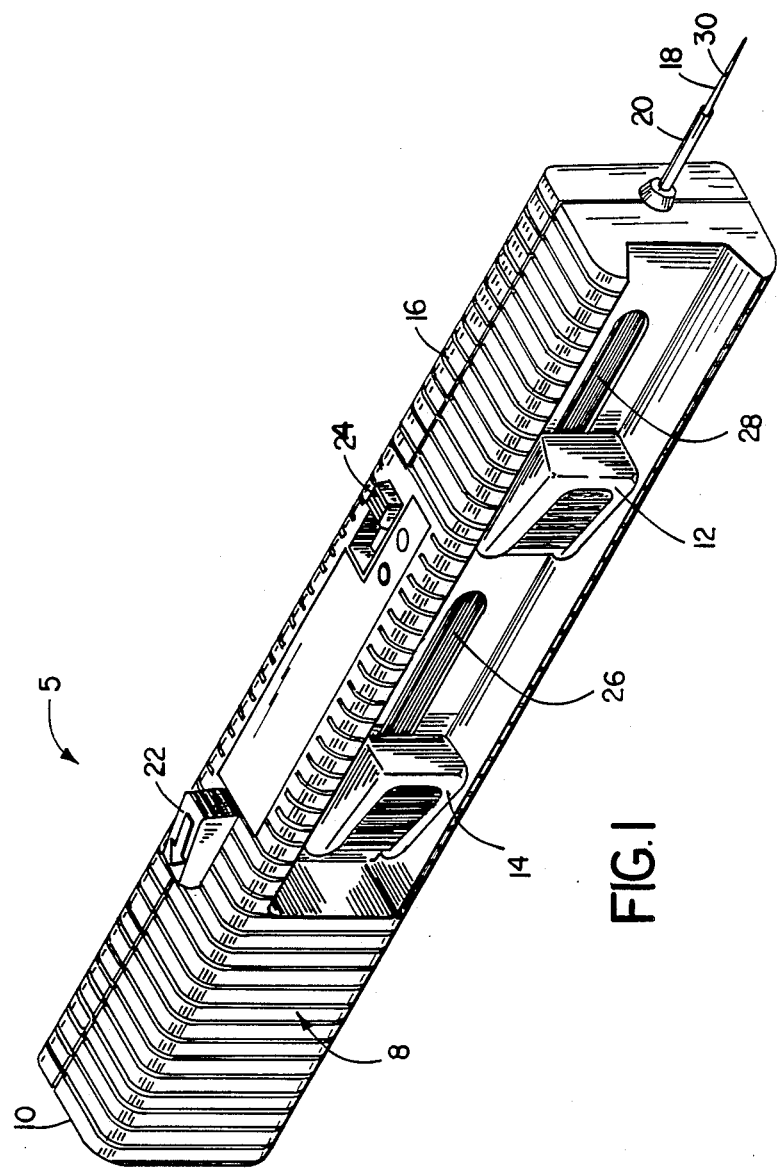
FIG. 1 is a perspective view of an embodiment of the biopsy needle instrument of the invention.

Referring to FIG. 1, a biopsy needle instrument 5 of the invention has a housing 8, consisting of an upper housing 10 and a lower housing 16. Stylet 18 and cannula 20 project from housing 8. Forward loading slide switch 12 and rearward loading slide switch 14 protrude from the upper housing and are constrained to move within slots 26, 28. A firing button 22 and a selector switch 24 also project from the housing 8.

Figure 1A:
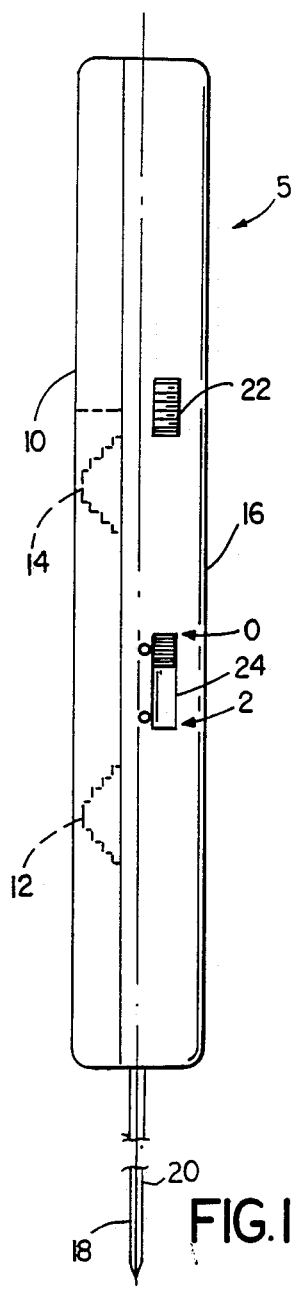

Referring to FIGS. 1(a) and (b), when the stylet 18 is to be loaded for firing, the rear loading slide switch 14, attached to the stylet 18, is slid rearwardly (arrow $R_R$) within a slot 26. When the stylet 18 is fired, the rear loading slide switch 14 moves forwardly within the slot.

Similarly, when the cannula 20 is to be loaded for firing, the forward loading slide switch 12, attached to the cannula 20, is slid rearwardly (arrow $F_R$) within slot 28. When the cannula 20 is fired, the forward loading slide switch 12 moves forwardly within the slot.

Figure 2:
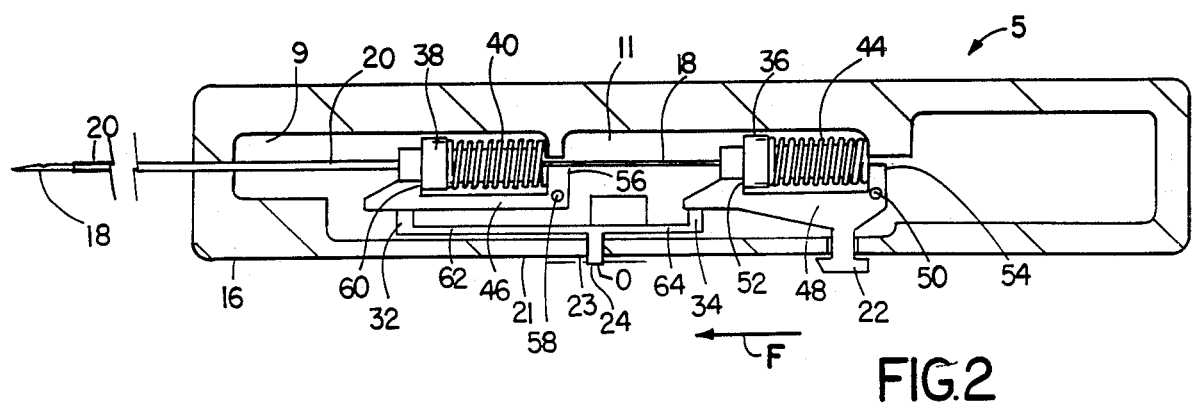

FIG. 2 shows the instrument firing mechanism positioned within the lower housing 16. Stylet 18 is located coaxially within cannula 20, and the forward end of each projects through the forward end of the lower housing 16. The rearward end of cannula 20 attaches to the cannula retaining collar 38 which is biased forward (arrow F) by spring 40. The cannula retaining collar 38 and spring 40 are located within a forward cavity 9 of the lower housing 16. The rearward end of the spring 40 rests against the rear lever 56 of the forward rocker arm 46 and is held in the compressed state by engagement of the cannula retaining collar 38 by the latch portion 60 of the forward rocker arm 46. The forward rocker arm 46 is prevented from pivoting about the pin 58 (thereby releasing cannula retaining collar 38 and spring 40) when the selector switch 24 is in the position designated as "0" by a forward restraining projection 32 of forward arm 62 of the selector switch 24.

The rearward end of the stylet 18 extends through cannula 20, cannula retaining collar 38, and spring 40 and is attached to a stylet retaining collar 36 which is biased forward (arrow F) by spring 44. The stylet retaining collar 36 and spring 44 are located within a rearward cavity 11 of the lower housing 16. The rearward end of spring 44 rests against the rear lever 54 of the rearward rocker arm 48 and is held in the compressed state by engagement of the stylet retaining collar 36 by the latch portion 52 of the rearward rocker arm 48. The rearward rocker arm 48 is prevented from pivoting about the pin 50 (and thereby releasing stylet retaining collar 36 and spring 44) when the selector switch 24 is in the position designated as "0" by a rearward restraining projection 34 of the rearward arm 64 of the selector switch 24.

As the selector switch 24 is moved forward to the position designated "2", the forward restraining projection 32 is moved forward away from the forward rocker arm 46. Rear restraining projection 34 is simultaneously move forward away from the rearward rocker arm 48. The rearward rocker arm 48 is thus free to pivot counterclockwise (arrow P) about pin 50. The forward rocker arm 46 is also free to pivot counterclockwise.

Operation

Figure 1B:
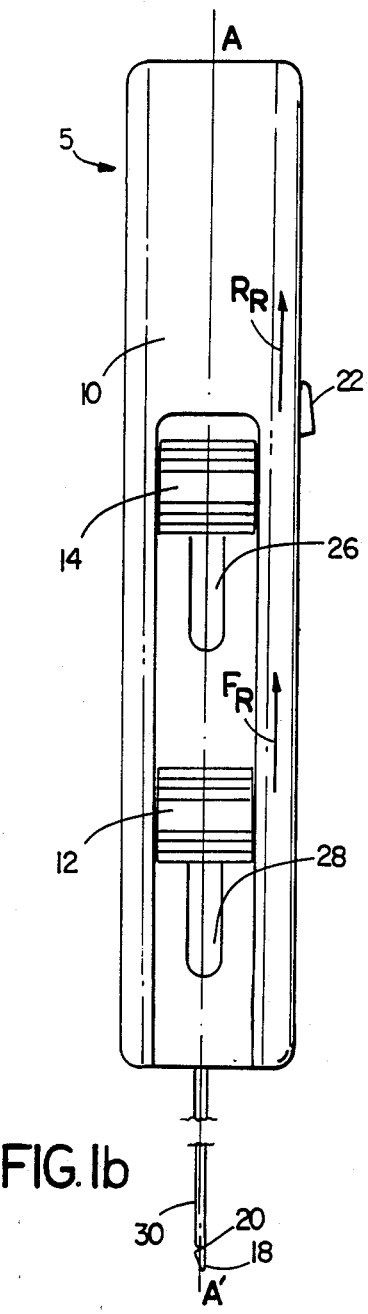
FIG. 1b is a top view of the instrument of FIG. 1.
Figure 3A:
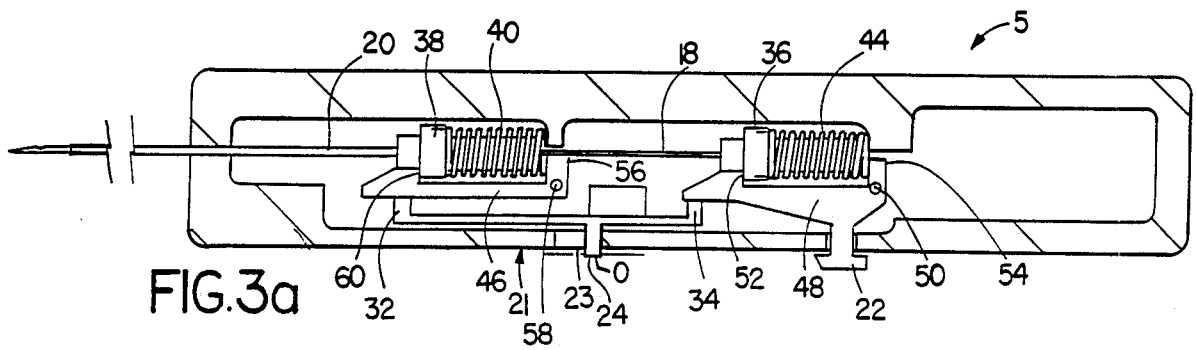
FIG. 3a is a cross-sectional view of the instrument of FIG. 2 with the selector switch set to a first safety position.

Referring also to FIG. 3a et seq. and FIG. 1b, with the selector switch 24 placed in position "2" (FIG. 3d), the cannula 20 is loaded by moving the front loading slide switch 12 rearwardly (arrow $F_R$). The front loading slide switch 12 is attached to the cannula retaining collar 38, and as the front loading slide switch is moved rearwardly, the cannula retaining collar 38 is also moved rearwardly and spring 40 is compressed. The compression puts pressure against rear lever 56 of the forward rocker arm 46 causing it to rotate clockwise (arrow $C_F$) about pin 58. This also causes the forward rocker arm 46 to rotate clockwise until the latch portion 60 of the forward rocker arm 46 engages the cannula retaining collar 38. At this point the cannula 20 is loaded for firing.

The stylet 18 is then loaded by moving the rear loading slide switch 14 rearwardly (arrow $R_R$). The rear loading slide switch 14 is attached to the stylet retaining collar 36, and as the rear loading slide switch 14 is moved rearwardly, spring 44 is compressed. The compression puts pressure against rear lever 54 of the rearward rocker arm 48 causing it to rotate clockwise (arrow $C_R$) about pin 50. This also causes the rearward rocker arm 48 to rotate clockwise until the latch portion 52 of the rearward rocker arm 48 engages the stylet retaining collar 36. At this point the stylet 18 is also loaded for firing. The selector switch is then moved to position "0" (FIG. 3a) so the restraining projections 32 and 34 of the selector switch 24 prevent the cannula 20 and stylet 18 respectively from being accidentally fired.

A benefit of the separately loadable cannula and stylet is that to load the device, only one spring need be compressed at a time, thereby significantly reducing the amount of effort required.

Figure 3B:
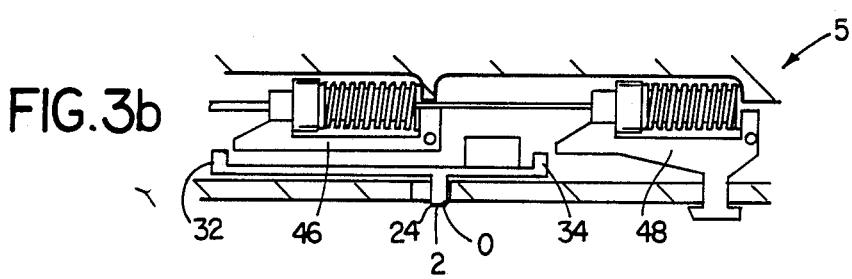
FIG. 3b is the cross-sectional view of the firing mechanism of the instrument of FIG. 3a with the selector switch set to project both the stylet and the cannula.

Referring to FIG. 3b, to fire the stylet 18 and the cannula 20 in quick succession, the selector switch 24 is moved forward to position "2", moving the restraining projections 32, 34 forward away from the rocker arms 46, 48 respectively. In this position both the forward 46 and rearward 48 rocker arms can rotate freely about the pins 58 and 50 respectively.

Figure 3C:
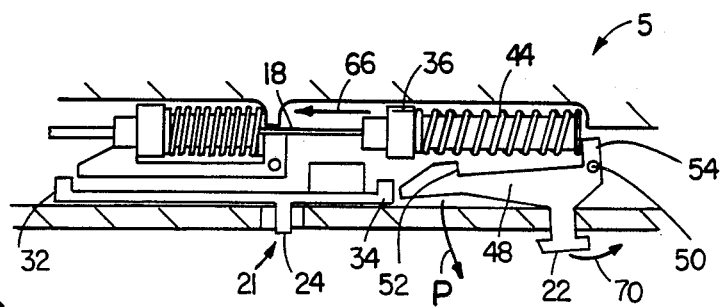
FIG. 3c is a similar view with the stylet firing.

Referring to FIG. 3c, when the firing button 22 is pressed rearwardly (arrow R), the rocker arm 48 rotates counter-clockwise (arrow $P_R$) about pin 50 causing latch portion 52 of the rocker arm 48 to be pulled away from the stylet retaining collar 36. This allows spring 44 to expand and project the stylet retaining collar 36 and stylet 18 forward (arrow $E_R$).

Figure 3D:
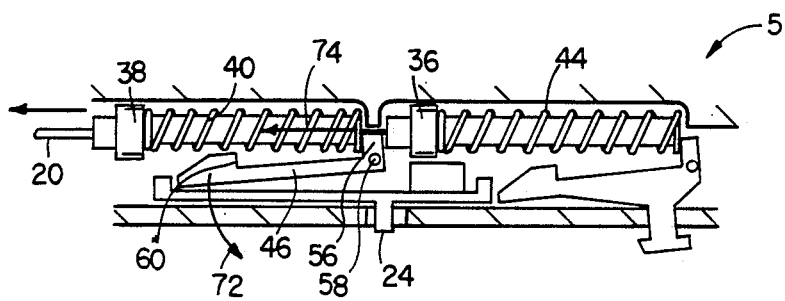
FIG. 3d is a similar view with the cannula firing.

Referring to FIG. 3d, as spring 44 expands, it propels the stylet retaining collar 36 against the rear lever 56 of the forward rocker arm 46. The momentum of the stylet retaining collar 36 forces the rear lever 56 forward (as shown by arrow 1) and causes forward rocker arm 46 to rotate counter clockwise (arrow $P_F$) about pin 58. As the rocker arm 46 rotates, it pulls the latch portion 60 of rocker arm 46 away from the cannula retaining collar 38. This releases the spring 40 and projects collar 38 and cannula 20 forward (arrow $E_F$).

Having shown an illustrative embodiment, those skilled in the art will realize many variations are possible which will still be within the scope and spirit of the claimed invention. Therefore, it is the intention to limit the invention only as indicated by the scope of the claims.

Other embodiments are within the following claims. For example, referring to FIG. 4a et seq. selector switch 24' has an additional intermediate position termed "1". In this embodiment, the forward arm 62' of the selector switch 24' is shorter than the forward arm 62 in the previously described embodiment so that when selector switch 24' is moved forward to the position "1" (FIGS. 4b and 4c), the rear restraining projection 34 is moved far enough forward so as to permit the rear rocker arm 48 to pivot about pin 50, while the forward restraining projection 32' still prevents the forward rocker arm 46 from pivoting about pin 58. As the selector switch 24 is moved further forward to the position designated as "2" (FIG. 4d), the forward restraining projection 32' moves further forward and away from the forward rocker arm 46 and permits the forward rocker arm 46 to pivot about pin 58.

To project the stylet 18 and the cannula 20 separately, the selector switch 24' is slid into the intermediate position, termed "1". This moves the rear restraining projection 34 forward of the rearward rocker arm 48 permitting the rearward rocker arm 48 to rotate counterclockwise (arrow $P_R$) about pin 50. However, due to the unequal length of the arms, the forward restraining projection 32' remains in a position to prevent rocker arm 46 from rotating counterclockwise (arrow $P_F$) about pin 58.

Referring to FIG. 4b, the stylet 18 is fired by pressing the firing button 22 rearwardly, (arrow R). Again this causes the rearward rocker arm 48 to rotate counterclockwise (arrow $P_R$) and move the latch portion 52 of the rearward rocker arm 48 away from the stylet retaining collar 36. This releases spring 44 which projects (arrow $E_R$) the stylet 18 and stylet retaining collar 36 forward.

Referring to FIG. 4c, when the stylet retaining collar 36 hits the rear lever 56 of the forward rocker arm 46, the rear lever 56 is prevented from moving by the forward restraining projection 32'. This then prevents the forward rocker arm 46 from rotating counterclockwise. At this point the stylet 18 is fully extended but the cannula 20 has not been fired.

To fire the cannula 20, the selector switch 24' is then moved into the position "2", moving the forward restraining projection 32' forward and away from the forward rocker arm 46. Although the cannula 20 may now be fired, it will not fire spontaneously because the compressive force of spring 40 exceeds the expansion force of spring 44 on the rearward lever 56 of the forward rocker arm 46. This force-couple attempts to cause the rocker arm 46 to rotate clockwise and to cause the rearward lever 56 of the forward rocker arm 46 also to rotate clockwise. Therefore the latch portion 60 of the forward rocker arm is held against the cannula retaining collar 38, holding the spring 40 in compression.

Referring to FIG. 4d, to fire the cannula 20, a forward force (arrow A) is applied to the rear loading slide switch 14. This forces the stylet retaining collar 36 further against the forward lever 56 and exceeds the compressive force of spring 40. This permits the forward rocker arm 46 to rotate counterclockwise (arrow $P_F$) away from the cannula retaining collar 38, releasing spring 40 and projecting the cannula retaining collar 38 and the cannula 20 forward.

To remove the biopsy sample once the cannula 20 has been fired, the cannula 20 and stylet 18 are withdrawn from the tumor and the cannula 20 is then retracted by rearwardly sliding the forward slide switch 12 to expose the tissue captured in the stylet notch 30 (FIG. 1c).

The benefit of the second embodiment is that if the stylet is projected and misses the tumor, the cannula need not be projected. The stylet can be reloaded separately and another attempt made to penetrate the tumor. In this way there is no unnecessary severing of healthy tissue by the cannula.

What is claimed is:

1. A biopsy needle instrument comprising:
   a housing defining a first cavity and a second cavity,
   extending from said housing, an axially elongated stylet having a distal end and a proximal end and defining a side-facing notch adjacent said distal end and a cannula coaxially disposed about said stylet, said cannula having a distal end and a proximal end,
   said stylet mounted for axial movement relative to said housing and relative to said cannula between a first, retracted position and a second, extended position,
   said cannula mounted for axial movement relative to said housing and relative to said stylet between a first, retracted position and a second, extended position,
   stylet retaining means at the proximal end of said stylet and disposed in said first cavity,
   cannula retaining means at the proximal end of said cannula and disposed in said second cavity,
   means for biasing said stylet distally toward said second, extended position,
   means for biasing said cannula distally toward said second, extended position,
   stylet latch means for retaining said stylet in said first, retracted position,
   cannula latch means for retaining said cannula in said first retracted position,
   means for retracting said stylet from said second, extended position to said first, retracted position for engagement of said stylet latch means to retain said stylet in retracted position against the means for biasing the stylet distally,
   separate and discrete means for retracting said cannula from said second, extended position to said first, retracted position for engagement of said cannula latch means to retain said cannula in retracted position against the means for biasing the cannula distally, and
   means for releasing said stylet latch means to allow said stylet to move from said first, retracted position to said second, extended position and thereafter releasing said cannula latch means to allow said cannula to move from said first, retracted position to said second, extended position.

2. The biopsy needle instrument of claim 1 further comprising a lock member adapted for movement between a first locking position and a second release position, said lock member in said first position disposed to oppose release of said stylet latch means and said cannula latch means, and said lock member, in said second, release position, removed from opposition to release of said stylet latch means and said cannula latch means.

3. The biopsy needle of claim 2 wherein said lock member is adapted for movement to a third, intermediate position, said lock member in said third position removed from opposition to release of said stylet latch means and disposed to oppose release of said cannula latch means.

4. The biopsy needle of claim 2 or 3 wherein said lock member comprises a slide element disposed for movement along an outer surface of said housing.

5. The biopsy needle of claim 1 wherein said bias means for said stylet comprises a compression spring.

6. The biopsy needle of claim 1 wherein said bias means for said cannula comprises a compression spring.

7. The biopsy needle of claim 1 wherein said stylet retaining means comprises a collar attached to said stylet and in communication with said stylet biasing means.

8. The biopsy needle of claim 1 wherein said cannula retaining means comprises a collar attached to said cannula and in communication with said cannula biasing means.

9. The biopsy needle of claim 1 wherein said stylet latch means for retaining said stylet in said first, retracted position, comprises a first rocker arm and a first pin, said first rocker arm adapted to rotate about said first pin between a first position and a second position, said first rocker arm, in said first position, adapted to engage said stylet retaining means and to retain said stylet in said first retracted position, and said first rocker arm, in said second position, spaced from engagement with said stylet retaining means.

10. The biopsy needle of claim 1 wherein said cannula latch means for retaining said cannula in said first retracted position, comprises a second rocker arm and a second pin, said second rocker arm adapted to rotate about said second pin between an first position and a second position, said second rocker arm, in said first position, adapted to engage said cannula retaining means to retain said cannula in said first retracted position, and said second rocker arm, in said second position, spaced from engagement with said cannula retaining means.

11. The biopsy needle of claim 1 wherein said means for retracting said stylet comprises a first slide switch slidably mounted upon and extending through said housing and attached to said stylet retaining means, such that when said first slide switch is moved rearwardly, said stylet retracts from said second extended position to said first retracted position.

12. The biopsy needle of claim 1 wherein said separate and discrete means for retracting said cannula comprises a second slide switch slidably mounted upon and extending through said housing and attached to said cannula retaining means, such that when said second slide switch is moved rearwardly, said cannula retracts from said second extended position to said first retracted position.

13. The biopsy needle of claim 1 wherein said means for releasing said stylet latch means comprises a button extending from said housing and attached to said stylet latch means, such that when said button is depressed, said stylet latch means ceases to retain said stylet.

14. A biopsy needle instrument comprising:
   a housing defining a first cavity and a second cavity,
   extending from said housing, an axially elongated stylet having a distal end and a proximal end and defining a side-facing notch adjacent said distal end and a cannula coaxially disposed about said stylet, said cannula having a distal end and a proximal end, said stylet mounted for axial movement relative to said housing and relative to said cannula between a first, retracted position and a second, extended position, said cannula mounted for axial movement relative to said housing and relative to said stylet between a first, retracted position and a second, extended position, stylet retaining means at the proximal end of said stylet and disposed in said first cavity, wherein said stylet retaining means comprises a collar attached to said stylet and in communication with said stylet biasing means, cannula retaining means at the proximal end of said cannula and disposed in said second cavity, wherein said cannula retaining means comprises a collar attached to said cannula and in communication with said cannula biasing means, means for biasing said stylet distally toward said second, extended position, wherein said bias means for said stylet comprises a compression spring, means for biasing said cannula distally toward said second, extended position, wherein said bias means for said cannula comprises a compression spring, stylet latch means for retaining said stylet in said first, retracted position, wherein said stylet latch means for retaining said stylet in said first, retracted position, comprises a first rocker arm and a first pin, said first rocker arm adapted to rotate about said first pin between a first position and a second position, said first rocker arm, in said first position, adapted to engage said stylet retaining means and to retain said stylet in said first retracted position, and said first rocker arm, in said second position, spaced from engagement with said stylet retaining means cannula latch means for retaining said cannula in said first retracted position, wherein said cannula latch means for retaining said cannula in said first retracted position, comprises a second rocker arm and a second pin, said second rocker arm adapted to rotate about said second pin between an first position and a second position, said second rocker arm, in said first position, adapted to engage said cannula retaining means to retain said cannula in said first retracted position, and said second rocker arm, in said second position, spaced from engagement with said cannula retaining means, means for retracting said stylet from said second, extended position to said first, retracted position for engagement of said stylet latch means to retain said stylet in retracted position against the means for biasing the stylet distally, wherein said means for retracting said stylet comprises a first slide switch slidably mounted upon and extending through said housing and attached to said stylet retaining means, such that when said first slide switch is moved rearwardly, said stylet retracts from said second extended position to said first retracted position, separate and discrete means for retracting said cannula from said second, extended position to said first, retracted position for engagement of said cannula latch means to retain said cannula in retracted position against the means for biasing the cannula distally, wherein said separate and discrete means for retracting said cannula comprises a second slide switch slidably mounted upon and extending through said housing and attached to said cannula retaining means, such that when said second slide switch is moved rearwardly, said cannula retracts from said second extended position to said first retracted position means for releasing said stylet latch means to allow said stylet to move from said first, retracted position to said second, extended position and thereafter releasing said cannula latch means to allow said cannula to move from said first, retracted position to said second, extended position, wherein said means for releasing said stylet latch means comprises a button extending from said housing and attached to said stylet latch means, such that when said button is depressed, said stylet latch means ceases to retain said stylet, and a lock member adapted for movement between a first locking position and a second release position, said lock member in said first position disposed to oppose release of said stylet latch means and said cannula latch means, and said lock member, in said second, release position, removed from opposition to release of said stylet latch means and said cannula latch means, wherein said lock member comprises a slide element disposed for movement along an outer surface of said housing.

15. A method of taking a tissue sample comprising the steps of:

providing a biopsy needle instrument comprising a housing defining a first cavity and a second cavity, extending from said housing, an axially elongated stylet having a distal end and a proximal end and defining a side-facing notch adjacent said distal end and a cannula coaxially disposed about said stylet, said cannula having a distal end and a proximal end, said stylet mounted for axial movement relative to said housing and relative to said cannula between a first, retracted position and a second, extended position, said cannula mounted for axial movement relative to said housing and relative to said stylet between a first, retracted position and a second, extended position, stylet retaining means at the proximal end of said stylet and disposed in said first cavity, cannula retaining means at the proximal end of said cannula and disposed in said second cavity, means for biasing said stylet distally toward said second, extended position, means for biasing said cannula distally toward said second, extended position, stylet latch means for retaining said stylet in said first, retracted position, cannula latch means for retaining said cannula in said first retracted position, means for retracting said stylet from said second, extended position to said first, retracted position for engagement of said stylet latch means to retain said stylet in retracted position against the means for biasing the stylet distally, separate and discrete means for retracting said cannula from said second, extended position to said first, retracted position for engagement of said cannula latch means to retain said cannula in retracted position against the means for biasing the cannula distally, and means for releasing said stylet latch means to allow said stylet to move from said first, retracted position to said second, extended position and thereafter releasing said cannula latch means to allow said cannula to move from said first, retracted position to said second, extended position, placing said locking member in a second release position, retracting said stylet from a second, extended position to a first, retracted position, retracting said cannula from a second, extended position to a first, retracted position, placing said locking member in a first locking position, positioning said stylet so as to allow said stylet to project into the tissue to be sampled, placing said locking member in said second release position, releasing said stylet to allow said stylet to move from said first, retracted position to said second, extended position and thereafter releasing said cannula to move from said first, retracted position to said second, extended position, thereby severing a sample of tissue; and withdrawing said stylet and cannula together from the tissue.

* * * * *